(12) United States Patent
Sheng

(10) Patent No.: US 9,913,689 B2
(45) Date of Patent: Mar. 13, 2018

(54) BREAST SUPPORT AND IMMOBILIZATION DEVICE FOR RADIOTHERAPY

(71) Applicant: The Regents Of The University Of California, Oakland, CA (US)

(72) Inventor: Ke Sheng, Los Angeles, CA (US)

(73) Assignee: THE REGENTS OF THE UNIVERSITY OF CALIFRONIA, Oakland, CA (US)

(*) Notice: Subject to any disclaimer, the term of this patent is extended or adjusted under 35 U.S.C. 154(b) by 288 days.

(21) Appl. No.: 14/441,152

(22) PCT Filed: Nov. 6, 2013

(86) PCT No.: PCT/US2013/068755
§ 371 (c)(1),
(2) Date: May 6, 2015

(87) PCT Pub. No.: WO2014/074602
PCT Pub. Date: May 15, 2014

(65) Prior Publication Data
US 2015/0272682 A1    Oct. 1, 2015

Related U.S. Application Data

(60) Provisional application No. 61/724,240, filed on Nov. 8, 2012.

(51) Int. Cl.
*A61B 19/00* (2006.01)
*A61B 90/17* (2016.01)
(Continued)

(52) U.S. Cl.
CPC ............ *A61B 19/203* (2013.01); *A61B 90/14* (2016.02); *A61B 90/17* (2016.02); *A61B 90/10* (2016.02); *A61N 2005/1097* (2013.01)

(58) Field of Classification Search
CPC ......... A61B 90/00; A61B 90/10; A61B 90/14; A61B 90/17; A61M 1/06; A61M 1/064
(Continued)

(56) References Cited

U.S. PATENT DOCUMENTS 6,122,542 A    9/2000 Lee et al.
6,146,377 A    11/2000 Lee et al.
(Continued)

FOREIGN PATENT DOCUMENTS

WO    2014/074602    5/2014

OTHER PUBLICATIONS

International Search Report and Written Opinion—PCT/US2013/068755—ISA/KR—dated Feb. 7, 2014.
(Continued)

*Primary Examiner* — Keri J Nelson
(74) *Attorney, Agent, or Firm* — Quarles & Brady LLP

(57) ABSTRACT

A comfortable, light weight device to properly position and elongate breast tissue for extended periods of time during radiotherapy and other medical procedures. In one embodiment, the breast fixation device is a generally cylindrical inflatable enclosure that wraps around the breast tissue. In another embodiment, the breast fixation device is composed of multiple rings that are placed around the breast tissue and inflated. In a further embodiment, the breast fixation device consists of multiple inflatable fingers which drape around the breast tissue and then squeeze the breast tissue into an elongated position as they are inflated.

29 Claims, 11 Drawing Sheets

(51) Int. Cl.
    *A61B 90/14*       (2016.01)
    *A61B 90/10*       (2016.01)
    *A61N 5/10*        (2006.01)

(58) Field of Classification Search
    USPC .................................... 128/845, 846, 869
    See application file for complete search history.

(56) References Cited

U.S. PATENT DOCUMENTS

| | | |
|---|---|---|
| 6,273,868 B1 | 8/2001 | Nordvik |
| 6,676,610 B2 * | 1/2004 | Morton ................ A61B 5/6834 |
| | | 600/573 |
| 6,802,808 B2 * | 10/2004 | Brady .................... A61B 5/053 |
| | | 600/29 |
| 2004/0073106 A1 | 4/2004 | Lee et al. |
| 2004/0215101 A1 | 10/2004 | Rioux et al. |

OTHER PUBLICATIONS

International Preliminary Report on Patentability—PCT/US2013/068755, The International Bureau of WIPO—Geneva, Switzerland, dated May 21, 2015.

* cited by examiner

BREAST SUPPORT AND IMMOBILIZATION DEVICE FOR RADIOTHERAPY

CROSS REFERENCE TO RELATED APPLICATIONS

This application is a national phase of PCT application PCT/US13/68755, filed on Nov. 6, 2013, under 35 U.S.C. § 371 and claims benefit of U.S. provisional application 61/724,240, filed Nov. 8, 2012, the disclosure of which is hereby incorporated herein in its entirety by reference.

FIELD OF THE INVENTION

The present invention relates to devices for advantageously supporting women's breasts during breast cancer radiotherapy and other medical procedures. More specifically, inflatable, lightweight, easy-to-use devices are provided to elongate and immobilize breast tissue.

BACKGROUND OF THE INVENTION

In 2011, an estimated 230,480 new cases of invasive breast cancer were expected to be diagnosed in the U.S. and 39,520 women were expected to die from the disease. The standard care for these patients is surgery followed by radiotherapy, which has been shown to significantly decrease the risk of loco-regional tumor recurrence.

Modern radiotherapy is known for its extremely high geometrical accuracy targeting at the tumors. For most cancers treated by radiotherapy, an accuracy of 3 mm is achieved. However, the accuracy of breast treatment is an order of magnitude worse due to poor set up and immobilization techniques. Breast setup and immobilization have been a persistent problem. The challenge can be appreciated from FIGS. 1A and 4A showing breast tissue when a patient is set up in the supine position without any form of breast support. The breast tissue is naturally pulled towards the patient chest by gravity. In order to treat the breast using a whole breast irradiation technique, the radiation field has to cover the entire volume marked by the intersecting line, including part of the heart and the lung. The over inclusiveness of the radiated tissue could lead to severe long term side effects. For example, the skin fold, where the pendulous breast is in contact with the chest skin, will receive a full dose from the radiation treatment, resulting in painful skin erythema and long term side effects as shown in FIG. 2A. Due to the uncertainty in the breast shape and position, a large geometrical margin has to be used that leads to increased normal breast tissue dose in partial breast irradiation method. This additional margin requirement necessitates treatment of larger volumes of normal breast tissue and recent reports have suggested that external beam partial breast irradiation may be associated with increased toxicity, specifically subcutaneous fibrosis and suboptimal cosmetic outcome (FIG. 2B).

In FIGS. 1B and 4B, a breast is shown in the prone position without any form of breast support. Radiotherapy in the prone position can improve the radiation dosimetry. The advantages are obvious that, due to the greater distance between the breast and patient body and the disappearance of mammary skin fold, lower toxicities to normal organs other than the breast are achievable. On the other hand, the prone position cannot be tolerated by many patients for repeating daily treatment. Also, the setup time is longer and the setup uncertainties are greater than treatments in the supine position. Furthermore, lymph nodes cannot be easily treated in this prone position. Due to these reasons, most patients will still be treated in the supine position that is associated with poor treatment accuracy and higher risk of severe toxicity.

A number of devices have been proposed to assist breast set up in the supine position. These devices include the breast thermoplastic cast shown in FIG. 3A. For this thermoplastic cast, the thermoplastic material is firm at room temperature but becomes moldable when heated up to 60° C. It can be then used to create masks that conform to patient breast contour. Thermoplastic masks are widely used in the immobilization of head and neck patients where sufficient bony structures can be immobilized by the mask. Its application in breast immobilization, though, has been unsuccessful due to the lack of rigidity in the breast tissue. It also increases radiation skin dose and leads to more severe skin reactions. A vendor has recently removed the thermoplastic cast product from their catalog.

A second type of existing breast support device for use in the supine position is the breast ring shown in FIG. 3B. The breast ring device consists of a reinforced polyvinylchloride tube formed into a ring that is placed around the breast. A strap around the patient's chest holds the ring in place. The breast ring provides very limited improvement in the breast position, though, at a cost of significantly higher skin dose at areas in contact with the ring. The breast ring idea was first published in 1994, but has never found much clinical acceptance.

A third type of existing breast support device is a plastic cup with or without vacuum as shown in FIG. 3C and described in U.S. Pat. Nos. 8,210,899; 7,742,796 and 7,597,104. Plastic cups with vacuum (i.e., suction cups) were experimented with as breast immobilization devices and found some success when the patient is not in the supine position. Breast tissue with suction cup support is shown in FIG. 4C. Nonetheless, the shear force applied on the skin would be too high to tolerate when the cups are used to lift the breast against gravity. As a result of these failed attempts, there are currently no viable commercial suction cup products. Typically, patients are either treated these days without any breast set up and immobilization device, or with improvised methods such as bubble wraps, tapes or straps that result in very poor positioning accuracy.

Other prior art efforts at breast immobilization are described in U.S. Pat. Nos. 6,418,188; 7,828,744; 7,489,761 and 6,146,377.

BRIEF SUMMARY OF THE INVENTION

The present invention provides a comfortable, light weight device to properly position breast tissue for extended periods of time during radiotherapy and other medical procedures, particularly when the patient is in the supine position. In its preferred embodiments, the breast fixation device of the present invention comprises one or more inflatable cylinders, rings or gripping fingers that wrap around the surface of the breast tissue. The breast fixation device is preferably formed from a lightweight polymer, such as medical grade polyethylene.

In one preferred embodiment, the breast fixation device takes the form of an airtight, inflatable polymeric enclosure having generally cylindrical interior and exterior walls. A hollow, generally cylindrical shaped interior cavity defined by the interior walls of the enclosure surrounds the breast tissue. To help maintain the generally cylindrical shape and provide the necessary breast support, the breast fixation device is preferably formed from a plurality of longitudinal sections.

In a first alternative embodiment, the breast fixation device consists of a plurality of inflatable concentric rings that are preferably connected together. To most effectively elongate and position the breast, each ring preferably has its own inflation valve so that the rings can be sequentially inflated starting with the ring closest to the patient's chest and proceeding outward. To achieve an optimal tilt to the breast after it has been elongated, one of the inflatable rings can be divided into sections having separate valves. By inflating some of the sections of this ring, but not others, the breast can be tilted to the desired orientation.

In a second alternative embodiment, the breast fixation device consists of a plurality of inflatable finger-like grippers. In this embodiment, the finger-like grippers are draped over the breast before being inflated. When the finger-like grippers are then inflated, they grab the surface of the breast and elongate the breast upward.

DETAILED DESCRIPTION OF THE INVENTION

Figure 1A:
FIG. 1A shows breast tissue when a patient is set up in the supine position without any form of breast support.
Figure 1B:
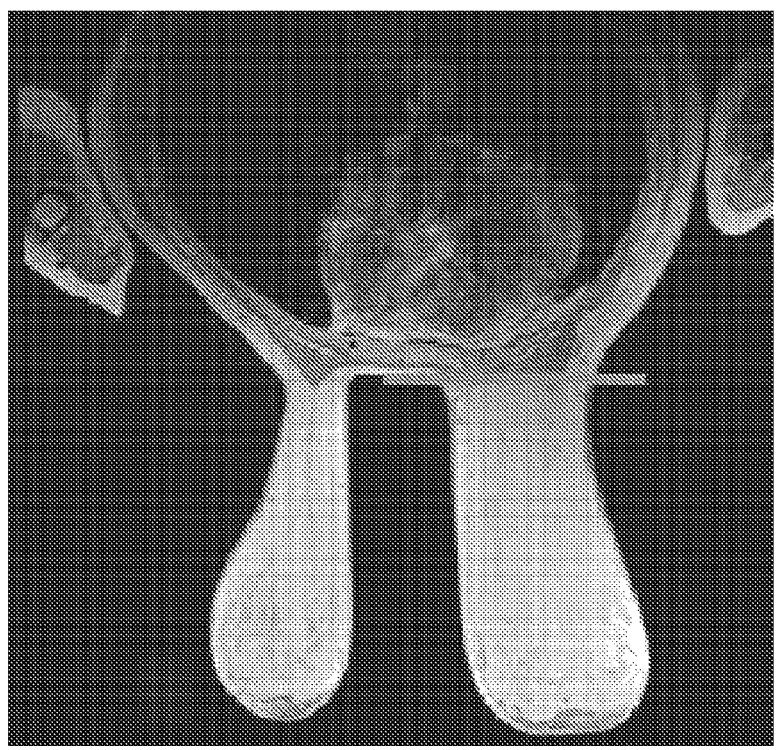
FIG. 1B shows breast tissue when a patient is set upon in the prone position without any form of breast support.
Figure 2A:
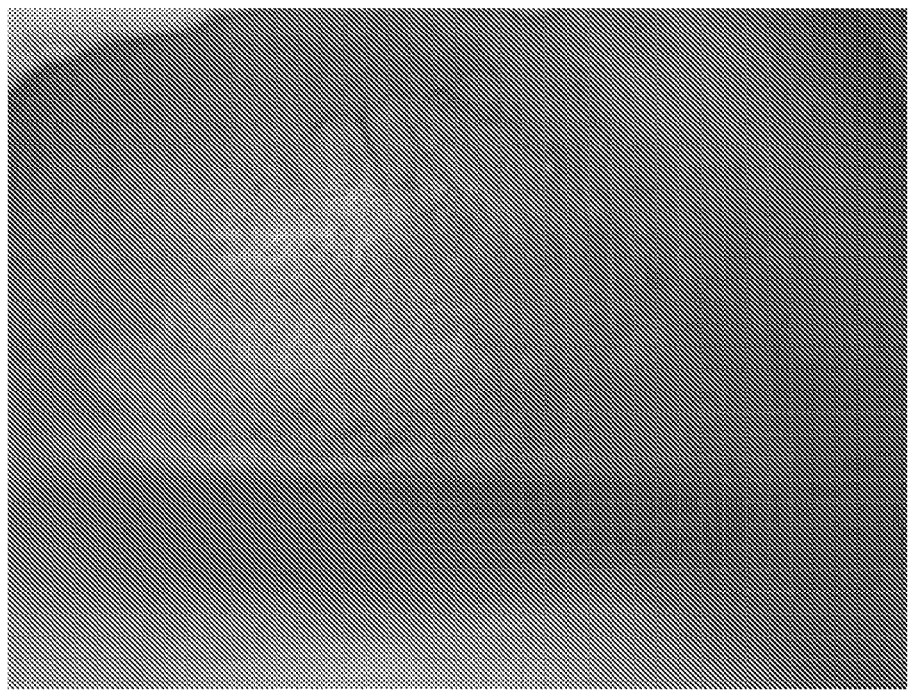
FIGS. 2A and 2B show long term effects of radiation therapy on breasts when the breasts are not properly supported and positioned.
Figure 2B:
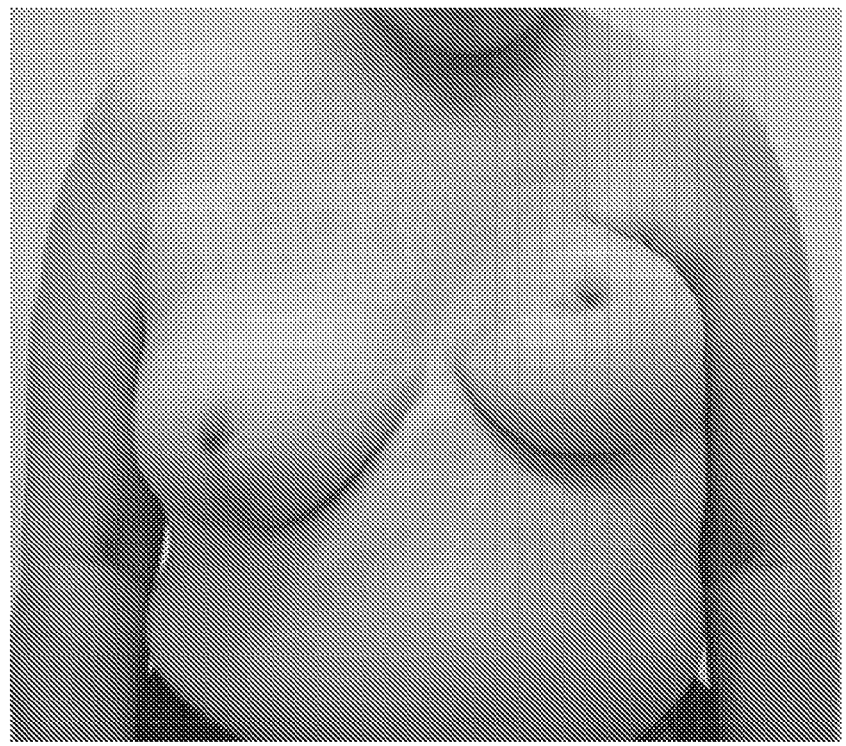
Figure 3A:
FIG. 3A shows a prior art thermoplastic cast.
Figure 3B:
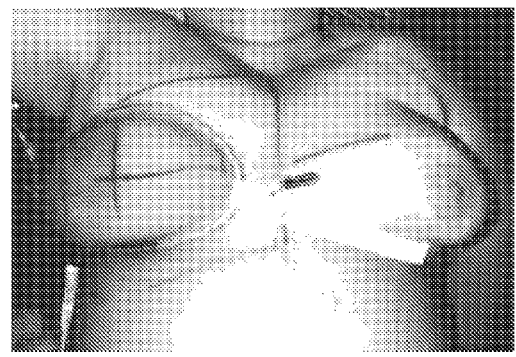
FIG. 3B shows a prior art breast ring.
Figure 3C:
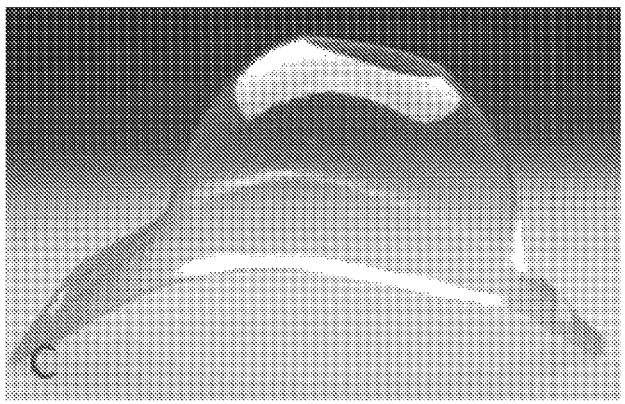
FIG. 3C shows prior art plastic breast cups.
Figure 3C:
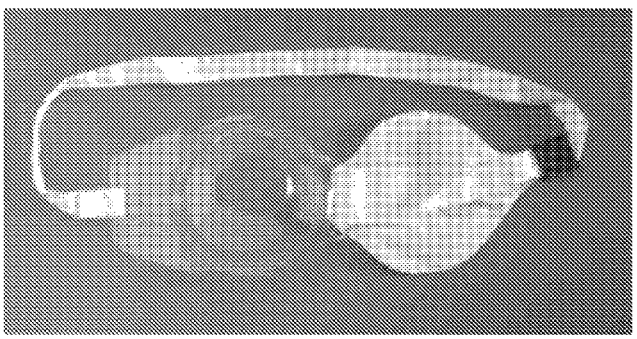
Figure 4A:
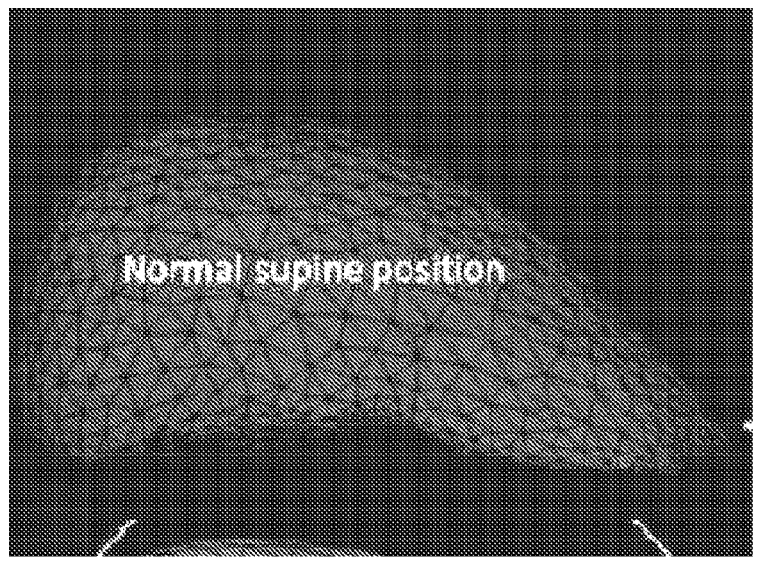
FIG. 4A shows a breast in a normal supine position.
Figure 4B:
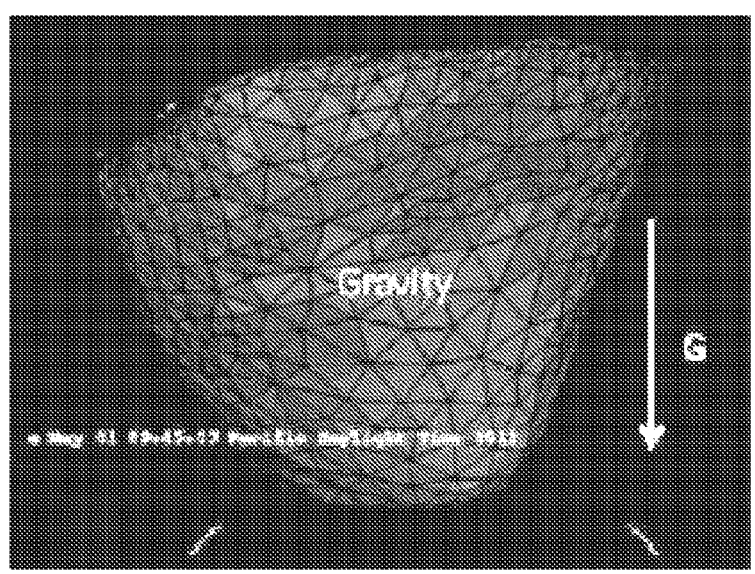
FIG. 4B shows a breast in a normal prone position.
Figure 4C:
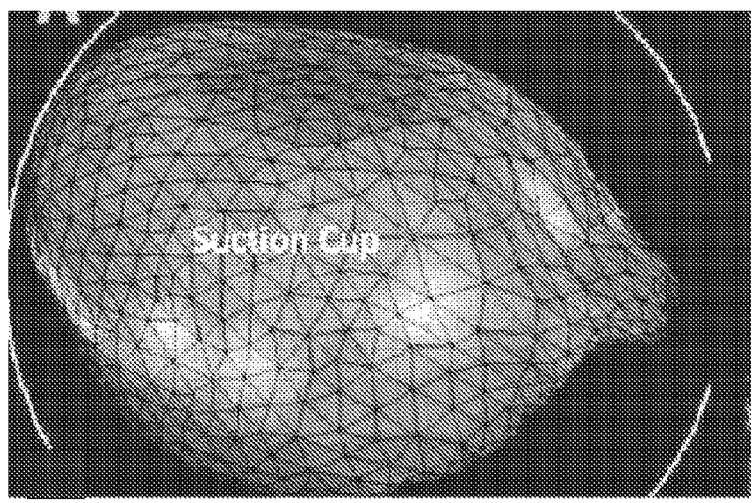
FIG. 4C shows a breast held within a plastic suction cup.
Figure 5A:
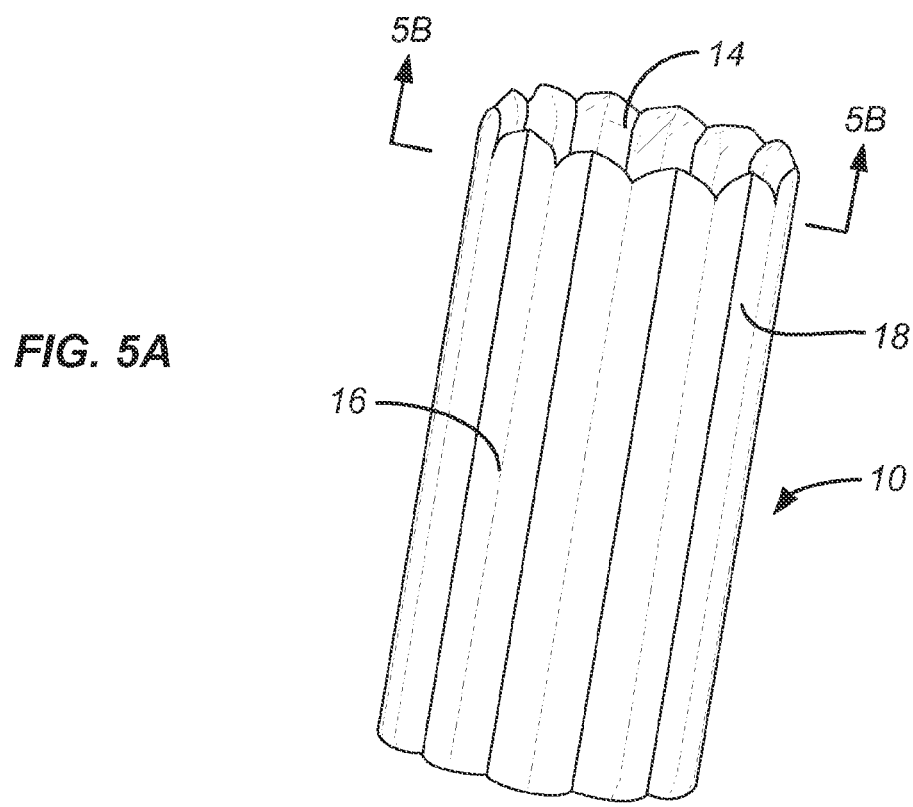
FIG. 5A shows a perspective view of a generally cylindrical breast fixation device of the present invention.
Figure 5B:
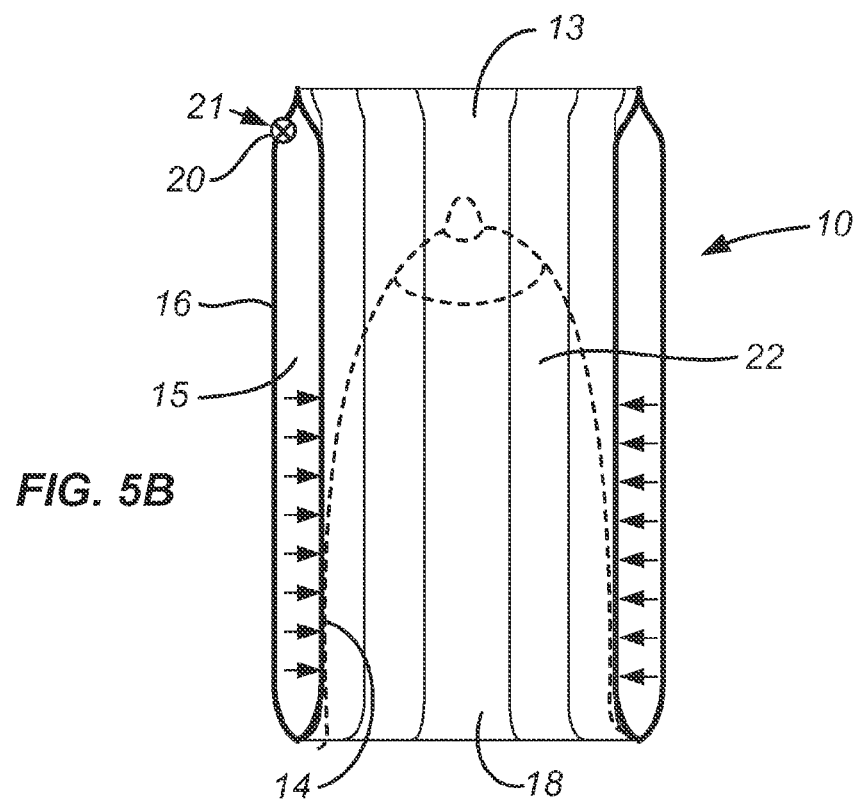
FIG. 5B shows a cross-sectional view of the generally cylindrical breast fixation device of FIG. 5A.

Referring now to FIGS. 5A and 5B, a preferred breast fixation device 10 of the present invention is shown. This breast fixation device 10 is preferably formed of a lightweight polymer, such as medical grade polyethylene, and has a generally cylindrical interior layer 14 as well as a generally cylindrical exterior layer 16. The thickness of the interior and exterior layers 14, 16 is preferably on the order of approximately 0.1 mm to 0.2 mm in order to keep the breast fixation device lightweight, while still providing sufficient strength and durability. The interior 14 and exterior 16 layers of the breast fixation device 10 form both an inflatable enclosure 15 and a hollow interior cavity 13.

In operation, the interior layer 14 of the breast fixation device 10 is placed around the patient's breast 22 before inflation. A pump (not shown), such as an electric or manual pump, is attached to valve 20, which is preferably a one-way valve. Air 21 is gradually pumped into breast fixation device 10 through valve 20 until the breast fixation device 10 is fully inflated. Preferably, the air fixation device 10 is inflated to a pressure on the order of approximately 12-15 psi. After radiation therapy is completed using one of the breast fixation devices of the present invention, a stem can be inserted into the valve 20 to deflate the breast fixation device or, alternatively, the breast fixation device can be removed by pealing it off the breast 22.

The breast fixation device 10 shown in FIGS. 5A and 5B has a generally cylindrical shape when full inflated with a hollow, generally cylindrical shaped inner cavity 13. In the illustrated embodiment, it is formed in a plurality of longitudinal sections 18. Nonetheless, as recognized by those of skill in the art, it could easily be formed without such sections 18. When a cylindrical breast fixation device 10 of the type shown in FIG. 5A is placed around a flaccid human breast 22 and inflated, it will elongate the breast 22 into a firmer, more stable position as shown in FIG. 5B so that the patient will be ready for radiation therapy. Since the breast fixation device 10 of the present invention is lightweight (i.e., similar to a balloon), it can be well tolerated by patients during radiation therapy procedures that often last for an hour or more.

A first alternative breast fixation device 30 of the present invention is shown in FIGS. 6A-6G. This breast fixation device 30 features multiple donut-shaped inflatable rings 32, 34, 36 and, optionally, a donut-shaped inflatable tilting ring 40. The rings 32, 34, 36, 40 are preferably interconnected with one another to form a hollow generally cylindrically shaped interior cavity 41. This first alternative breast fixation device 30 embodiment differs from the FIG. 5A embodiment by having the inflatable ring sections 32, 34, 36 positioned horizontally transverse to the breast tissue 22 rather than vertically parallel to the breast tissue 22. In the preferred embodiment, each inflatable ring 32, 34, 36 has a separate inflation valve 42, 44, 46, respectively. Having separate inflation valves 42, 44, 46 allows the rings to be inflated sequentially, rather than all at once. Like the FIG. 5A embodiment, the first alternative breast fixation device 30 is preferably formed of a lightweight polymer, such as medical grade polyethylene, having a thickness on the order of 0.1 mm to 0.2 mm.

Figure 6A:
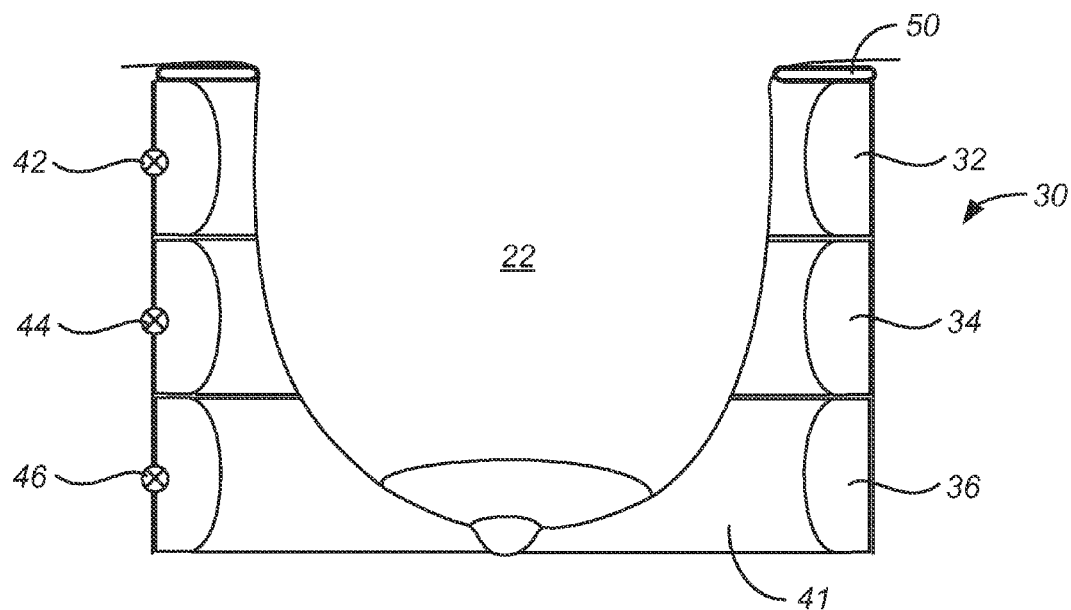
FIG. 6A shows a cross-sectional view before inflation of a first alternative breast fixation device of the present invention having inflatable rings.
Figure 6B:
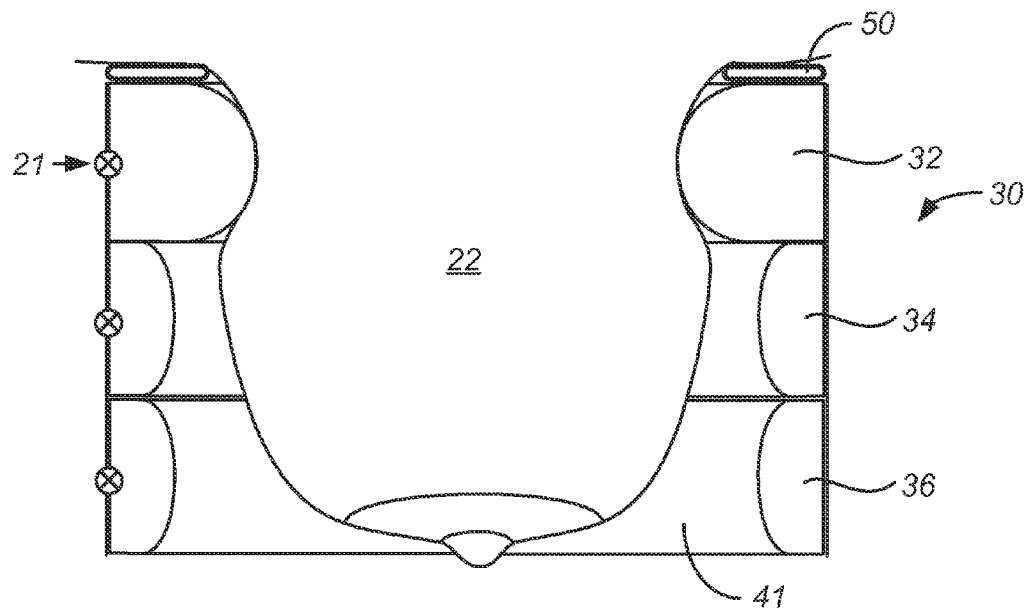
FIG. 6B shows the breast fixation device of FIG. 6A as the first ring is inflated.
Figure 6C:
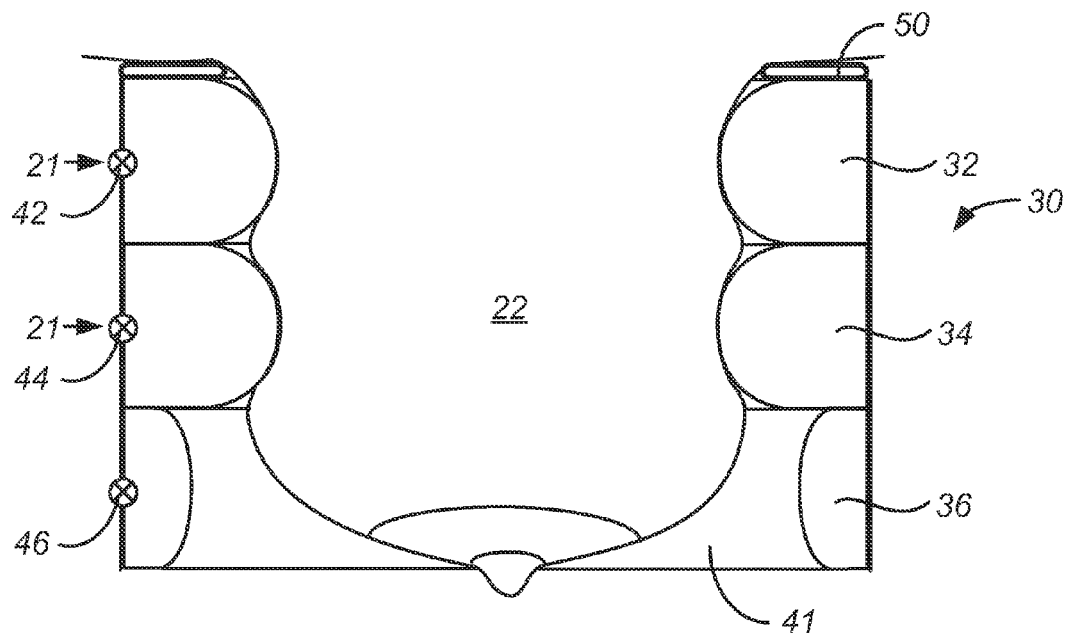
FIG. 6C shows the breast fixation device of FIG. 6A after the first and second rings are inflated.
Figure 6D:
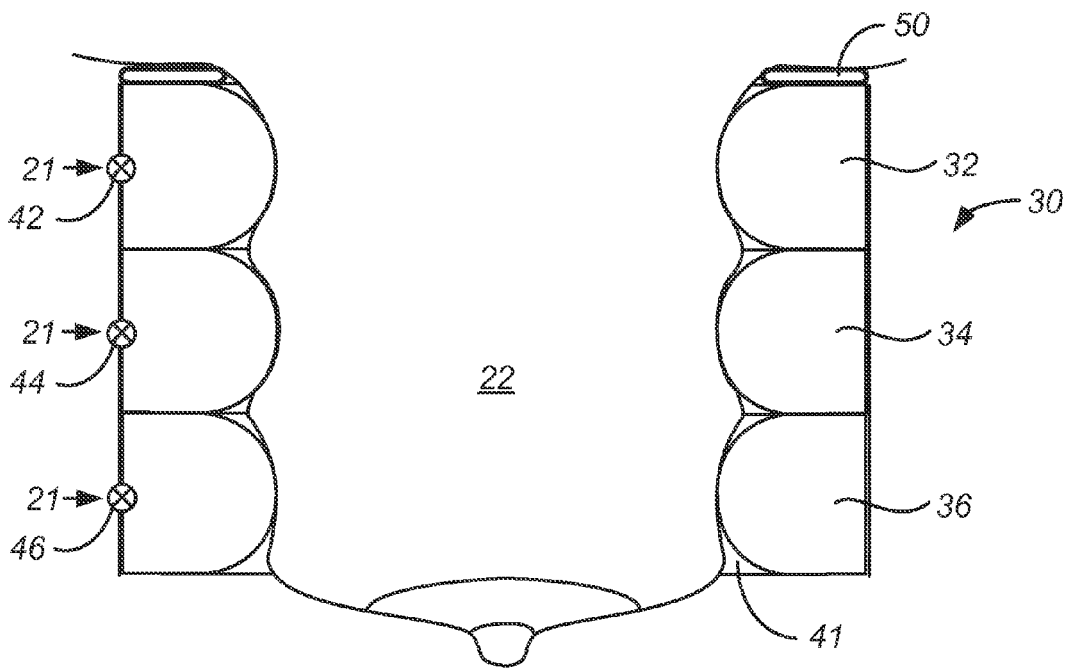
FIG. 6D shows the breast fixation device of FIG. 6A when all the rings are fully inflated.
Figure 6E:
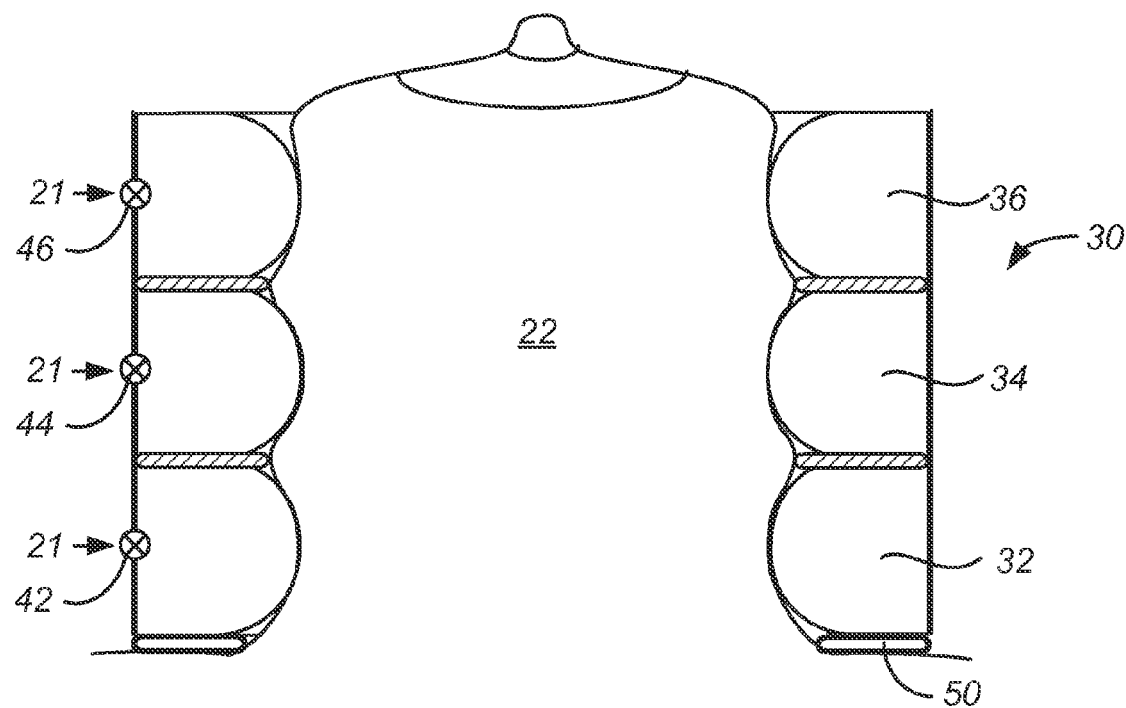
FIG. 6E shows the fully inflated breast fixation device of FIG. 6D when the patient has been moved from the prone position to the supine position.

FIG. 6A shows the first alternative breast fixation device 30 before any of the rings 32, 34, 36 have been inflated. To achieve the desired results, the patient is preferably first placed in the prone position so that the breast 22 is hanging downward. The inflatable ring 32 closest to the patient's chest is preferably inflated first, as shown in FIG. 6B. By inflating the ring 32 closest to the patient's chest first, the breast tissue 22 is urged into a more elongated, downward position. As shown in FIG. 6C, the adjacent ring 34 moving away from the patient's chest is inflated next. The ring 36 furthest away from the patient's chest is preferably inflated last, as shown in FIG. 6D. When all three rings 32, 34, 36 have been inflated as shown in FIG. 6D, the patient's breast is suitably immobilized for radiation therapy. As shown in FIG. 6E, the patient is then preferably moved from the prone position to the supine position to conduct the radiation therapy. Because of the breast fixation device 30 of the present invention, the breast 22 remains in an elongated, immobilized position even when the patient is moved from a prone position to a supine position. While the first alternative breast fixation device 30 is shown here with three inflation rings 32, 34, 36, those of skill in the art will recognize that a greater or lesser number of rings could also be used. Also, while separate valves 42, 44, 46 are shown in the illustrated embodiment to allow for sequential inflation of the rings 32, 34, 36, those of skill in the art will recognize that fewer or greater numbers of valves could also be used and still accomplish an elongated fixation of the breast tissue.

Figure 6F:
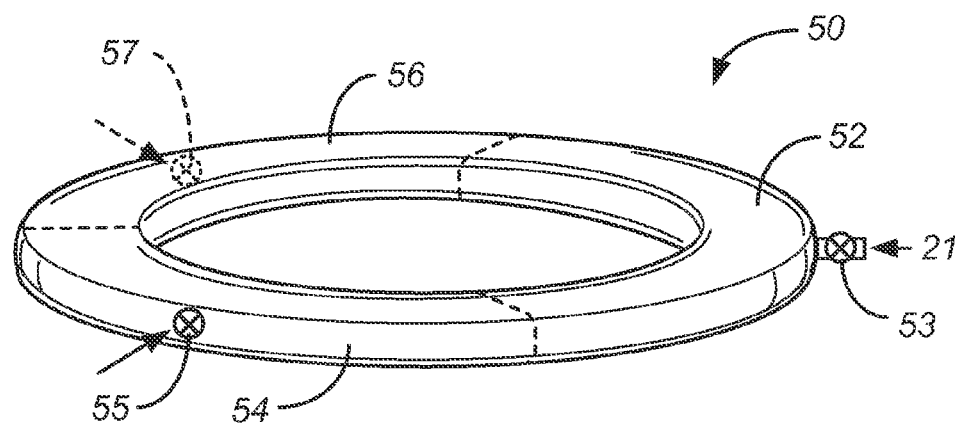
FIG. 6F show a perspective view of a breast tilt ring.
Figure 6G:
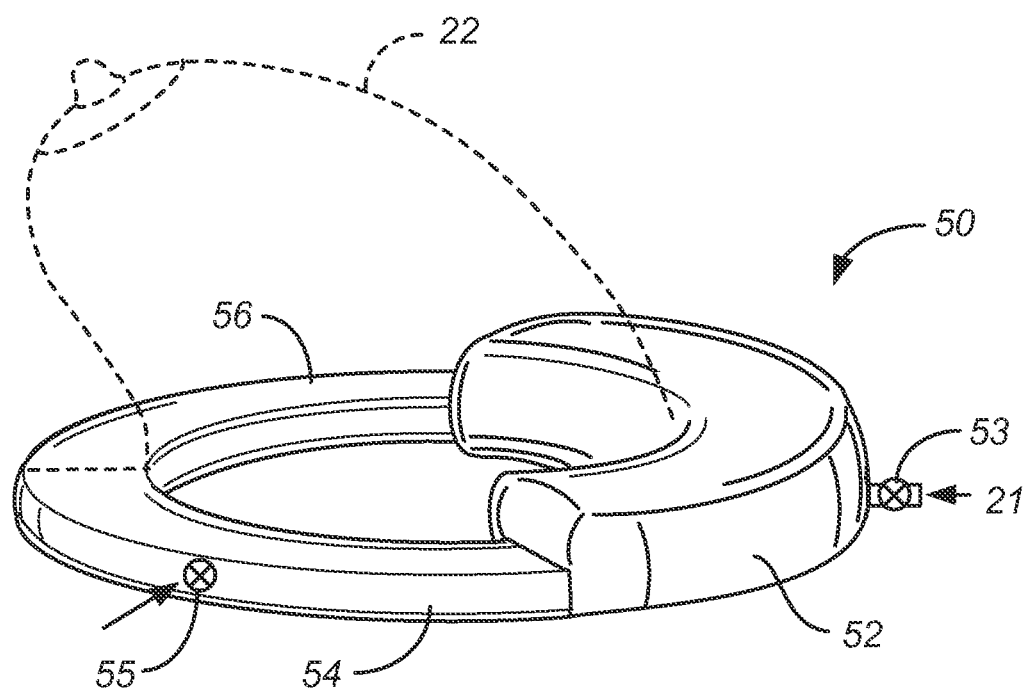
FIG. 6G shows how inflation of one section of the breast tilt ring of FIG. 6F, but not of the other sections, can tilt the breast tissue.

In addition to the inflatable rings 32, 34, 36, the first alternative breast fixation device also preferably includes a tilting ring 50. When the breast is immobilized by the inflatable rings 32, 34, 36, it may need to be tilted at a particular angle to achieve the best results during radiotherapy. The tilting ring 50 allows this tilting to occur. A close-up view of the tilting ring is shown in FIGS. 6F and 6G. In the preferred embodiment, the tilting ring 50 has three separately inflatable sections 52, 54, 56, each with its own inflation valve 53, 55, 57. As shown in FIG. 6G, when one of the tilting ring sections 52 is inflated, it will press against the breast 22 and tend to tilt it.

Figure 7A:
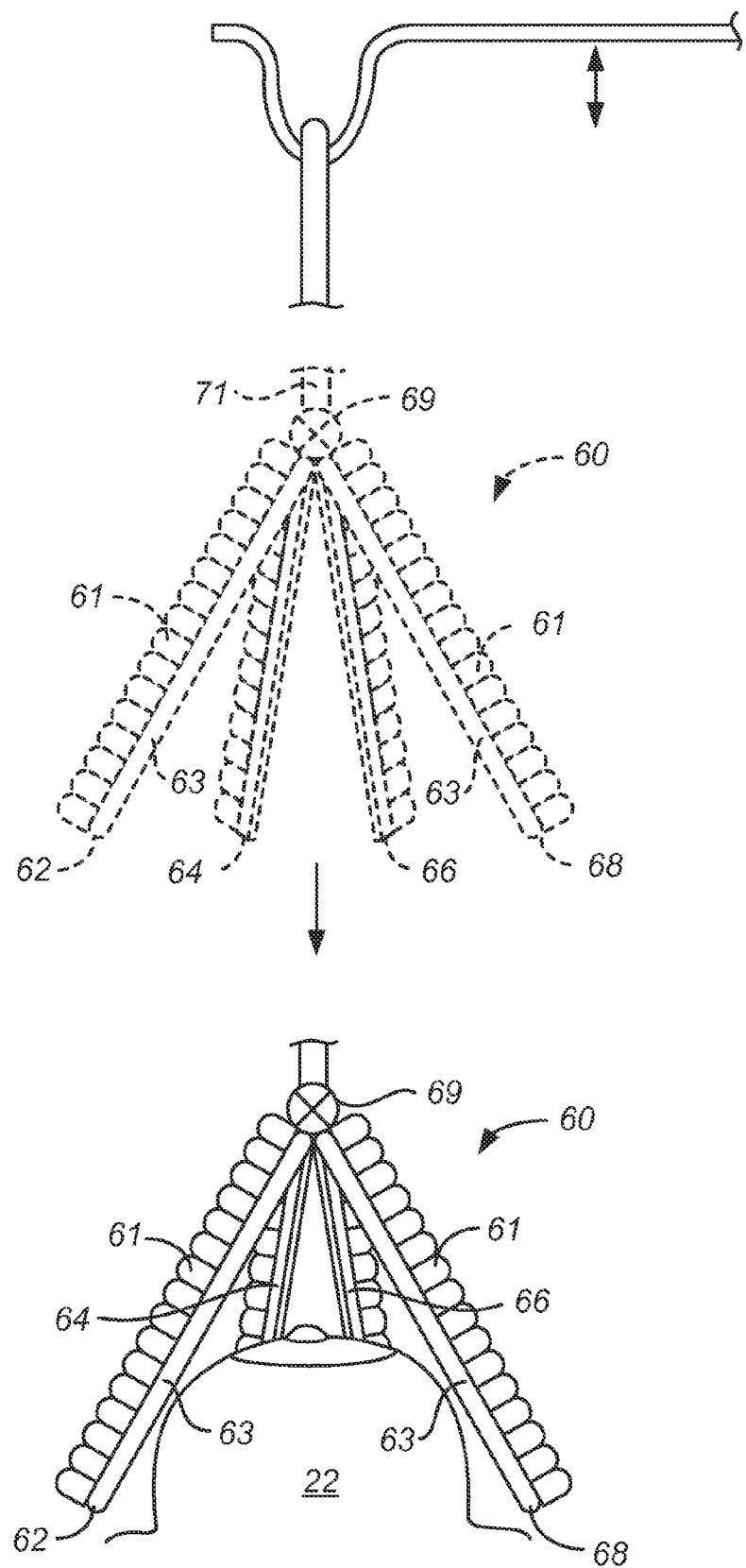
FIG. 7A shows a front view of a second alternative breast fixation device featuring multiple finger-like grippers.
Figure 7B:
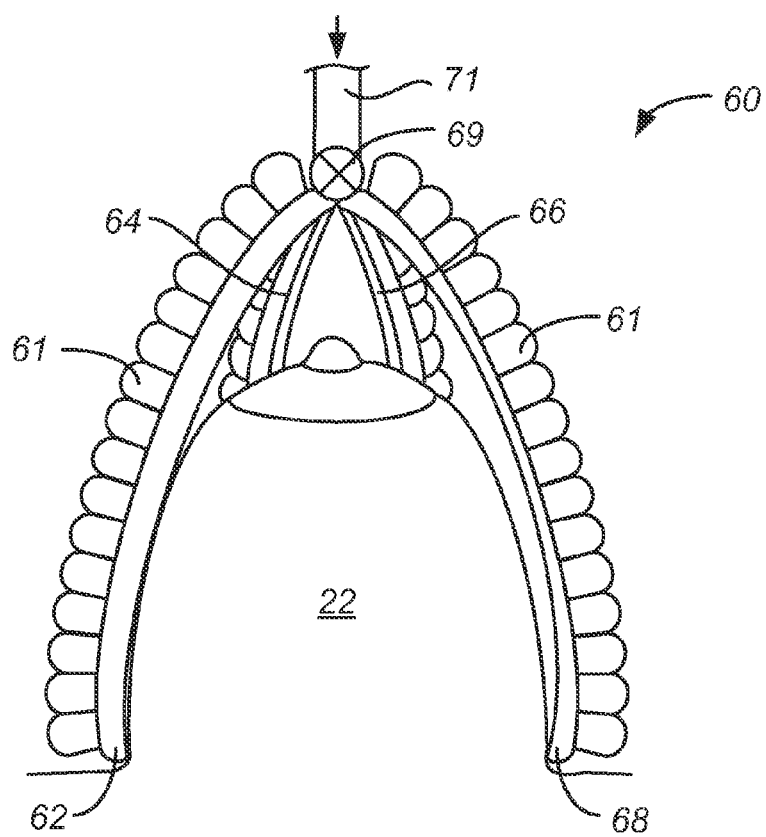
FIG. 7B shows the finger-like gripper embodiment of FIG. 7A as the finger-like grippers are being inflated.
Figure 7C:
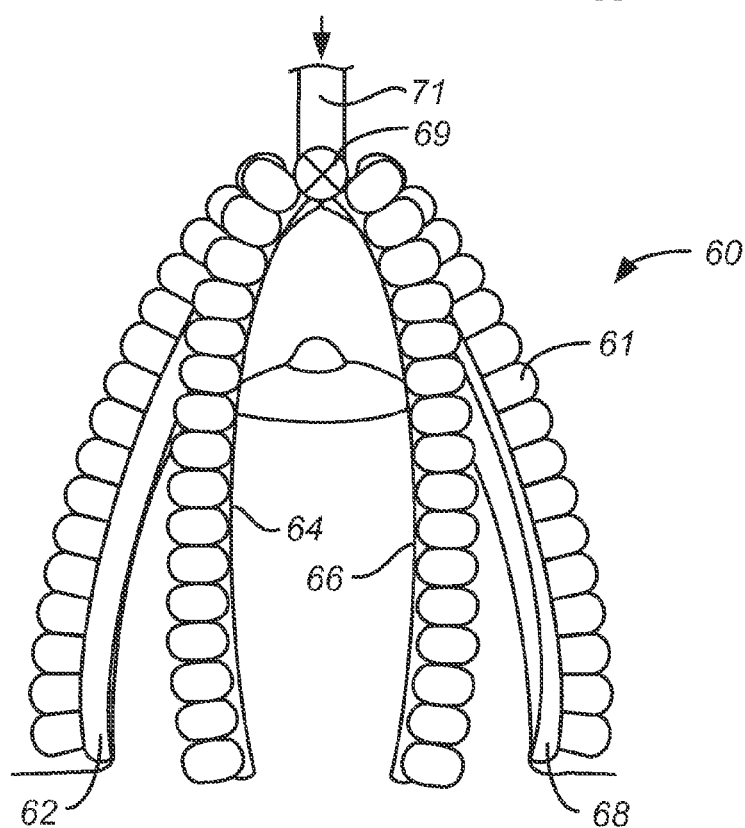
FIG. 7C shows the finger-like gripper embodiment of FIG. 7C when the finger-like grippers are fully inflated.

A second alternative breast fixation device 60 embodiment is shown in FIGS. 7A-7C. This breast fixation device 60 has a plurality of gripping fingers 62, 64, 66, 68 which can be draped on top of the breast as shown in FIG. 7A. In the illustrative embodiment, four gripping fingers 62, 64, 66, 68 are shown. Nonetheless, those of skill in the art will recognize that a different number of gripping fingers could be used, preferably ranging from four to ten gripping fingers. Each gripping finger 62, 64, 66, 68 preferably consists of an inflatable stem 63 and multiple bulbs 61 on the side of the stem 63 facing away from the breast 22. The stem 63 and bulbs 61 are preferably formed as an integral unit so that they can be inflated together. Moreover, the gripping fingers 62, 64, 66, 68 preferably have a common inflation valve 69 so that, when they are inflated, they are inflated simultaneously. As with the other breast fixation device embodiments 10, 30, the second alternative breast fixation device 60 is preferably formed from a lightweight polymer, such as medical grade polyethylene, having a thickness on the order of 0.1 mm to 0.2 mm. FIGS. 7B and 7C illustrates how the gripping finger breast fixation device 60 attaches to the patient's breast 22 and elongates it during inflation. Specifically, as the gripping finger bulbs 61 are inflated, they press against each other and cause the gripping fingers 62, 64, 66, 68 to curl around the breast 22 and thereby elongate the breast tissue upward. Since, in the preferred embodiment, all of the gripping fingers 62, 64, 66, 68 are inflated simultaneously through a single valve 69, the gripping fingers 62, 64, 66, 68 curl around the breast 22 symmetrically and at the same rate. This second alternative breast fixation device embodiment 60 has the advantage of allowing the patient to remain in the same position, such as the supine position, while the breast is being immobilized without the need to change to a different position. Preferably, the breast fixation device 60 is tethered by tube 71 to a vertically movable fixture 72 (FIG. 7A) so that the breast can be lifted after it is immobilized.

In the foregoing specification, the invention has been described with reference to specific preferred embodiments and methods. It will, however, be evident to those of skill in the art that various modifications and changes may be made without departing from the broader spirit and scope of the invention as set forth in the appended claims. For example, a strap may be used with one or more of the breast fixation devices of the present invention to better attach it to a patient's body. The specification and drawings are, accordingly, to be regarded in an illustrative, rather than restrictive sense.

What is claimed is:

1. A breast fixation device for immobilizing and elongating a human breast during medical procedures, the breast fixation device comprising:
   an airtight, inflatable, polymeric enclosure having generally cylindrical interior and exterior walls;
   a hollow, substantially cylindrical interior cavity defined by the interior walls of the enclosure and;
   an enclosure valve to allow air to be inserted into the enclosure, wherein the interior walls are sized such that substantially the entire human breast is confined within the interior cavity when the human breast is fully inserted into the interior cavity and the air is then inserted into the enclosure via the enclosure valve in order to compress the human breast with the interior walls and thereby elongate the human breast.

2. The breast fixation device of claim 1, wherein the interior cavity is sized to fit around the human breast and to allow the human breast to be elongated when the enclosure is inflated.

3. The breast fixation device of claim 1, wherein the enclosure is made from medical grade polyethylene having a thickness of between approximately 0.1 mm to 0.2 mm.

4. The breast fixation device of claim 1, wherein the enclosure is configured to be inflated to between approximately 12 and 15 psi.

5. The breast fixation device of claim 1, wherein the valve is a one-way valve.

6. The breast fixation device of claim 1, wherein interior walls have a length in a direction aligned with a nominal center axis of the substantially cylindrical interior cavity that is longer than an elongated length, in the same direction, of the human breast with which the breast fixation device is to be used.

7. The breast fixation device of claim 1, wherein (i) the interior cavity includes a length and a diameter, and (ii) the diameter of the interior cavity is substantially the same along the length of the interior cavity.

8. The breast fixation device of claim 1, wherein the enclosure is formed by a plurality of longitudinal sections extending parallel along a length of the enclosure.

9. The breast fixation device of claim 1, wherein the enclosure is configured such that that the interior cavity is substantially cylindrical when (i) the enclosure is inflated and (ii) the enclosure is deflated.

10. The breast fixation device of claim 9, wherein (i) the interior cavity includes a length, an inflation diameter and a deflation diameter, (ii) the inflation diameter is substantially the same along the length of the interior cavity when the enclosure is inflated, and (iii) the deflation diameter is substantially the same along the length of the interior cavity when the enclosure is deflated.

11. The breast fixation device of claim 1, wherein the interior cavity defines (i) a first open end for inserting the human breast into the interior cavity, and (ii) a second open end, opposite the first open end.

12. A breast fixation device for immobilizing and elongating a human breast during medical procedures, the breast fixation device comprising:
a plurality of inflatable donut-shaped polymeric rings interconnected to form a hollow, generally cylindrically shaped interior cavity, at least one of the plurality of inflatable donut-shaped polymeric rings divided into a plurality of separately inflatable sections and;
a valve in each of the rings to allow air to be inserted into each of the rings.

13. The breast fixation device of claim 12, wherein the interior cavity is sized to fit around the human breast and to cause the human breast to be elongated when the rings are inflated while the human breast is inserted within the interior cavity.

14. The breast fixation device of claim 12, wherein the rings are made from a medical grade polyethylene having a thickness of between approximately 0.1 mm and 0.2 mm.

15. The breast fixation device of claim 12, wherein each of the plurality of separately inflatable sections includes an inflation valve.

16. The breast fixation device of claim 15, wherein the sections of the at least one ring are arcuate sections that are arranged end-to-end to form the at least one ring.

17. The breast fixation device of claim 12, wherein the rings each have the same inner and outer diameters.

18. A breast fixation device for immobilizing and elongating a human breast during medical procedures, the breast fixation device comprising:
a plurality of airtight, inflatable, polymeric gripping fingers connected to each other at one end, wherein each of the gripping fingers includes an integrally formed stem and multiple bulbs; and
a valve positioned at the interconnection of the gripping fingers which, when air is inserted into the valve, allows the gripping fingers to be simultaneously inflated.

19. The breast fixation device of claim 18, wherein the gripping fingers are configured so that they can be draped over a human breast in a manner that allows them to grip and elongate the human breast when inflated.

20. The breast fixation device of claim 18, wherein the gripping fingers are made from a medical grade polyethylene having a thickness between approximately 0.1 mm and 0.2 mm.

21. The breast fixation device of claim 18, wherein the bulbs for each of the gripping fingers are arranged along the corresponding stem such that when the bulbs for one the gripping fingers are inflated, the bulbs for that gripping finger push against adjacent bulbs of that gripping finger and cause the stem of that gripping finger to flex.

22. The breast fixation device of claim 18, wherein the bulbs and the stem for each of the gripping fingers are configured to be in fluidic communication with one another such that the bulbs and the stem of each of the gripping fingers inflate simultaneously when air is inserted through the valve.

23. The breast fixation device of claim 18, wherein the breast fixation device includes between four and ten gripping fingers.

24. A method of immobilizing and elongating human breast tissue of a patient for a medical procedure, the method comprising the steps of:
placing an inflatable, polymeric breast fixation device around human breast tissue of the patient;
while the patient is in a prone position, inflating the breast fixation device through a valve in a manner which causes the breast fixation device to elongate and immobilize the human breast tissue of the patient; and
performing the medical procedure while the patient is in a supine position.

25. The method of claim 24 wherein:
the breast fixation device comprises an inflatable, polymeric enclosure having generally cylindrical interior and exterior walls, a hollow, generally cylindrically shaped interior cavity, and the valve;
the valve is configured to allow air to be inserted into the enclosure; and
the interior walls are sized such that substantially the entire human breast is confined within the interior cavity when the human breast is fully inserted into the interior cavity and the air is then inserted into the enclosure via the valve in order to compress the human breast with the interior walls and thereby elongate the human breast.

26. The method of claim 24, wherein the breast fixation device comprises:
a plurality of airtight, inflatable donut-shaped polymeric rings interconnected to form a hollow, generally cylindrically shaped interior cavity, and
a valve in each of the rings to allow air to be inserted into each of the rings.

27. The method of claim 26, further comprising sequentially inflating the rings while the rings are surrounding the breast tissue, starting with the ring closest to the patient's chest and ending with the ring furthest away from the patient's chest, wherein the rings are kept inflated during the inflation of subsequently-inflated rings.

28. The method of claim 24 wherein the breast fixation device comprises a plurality of airtight, inflatable, polymeric gripping fingers connected to each other at one end wherein each of the gripping fingers includes an integrally formed stem and multiple bulbs, and a valve positioned at the interconnection of the gripping fingers which, when air is inserted into the valve, allows the gripping fingers to be simultaneously inflated.

29. A breast fixation device for immobilizing and elongating a human breast during medical procedures, the breast fixation device comprising:
a plurality of inflatable donut-shaped polymeric rings interconnected to form a hollow, generally cylindrically shaped interior cavity;
a valve in each of the rings to allow that allows air to be inserted into each of the rings; and
wherein the rings each have the same inner and outer diameters.

* * * * *